US010951841B2

(12) United States Patent
Mizuno

(10) Patent No.: US 10,951,841 B2
(45) Date of Patent: Mar. 16, 2021

(54) IMAGE PROCESSING APPARATUS, IMAGE PROCESSING METHOD, AND ELECTRONIC APPARATUS

(71) Applicant: SONY SEMICONDUCTOR SOLUTIONS CORPORATION, Kanagawa (JP)

(72) Inventor: Hiroyuki Mizuno, Tokyo (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 0 days.

(21) Appl. No.: 16/495,504

(22) PCT Filed: Mar. 15, 2018

(86) PCT No.: PCT/JP2018/010162
§ 371 (c)(1),
(2) Date: Sep. 19, 2019

(87) PCT Pub. No.: WO2018/180528
PCT Pub. Date: Oct. 4, 2018

(65) Prior Publication Data
US 2020/0014865 A1 Jan. 9, 2020

(30) Foreign Application Priority Data

Mar. 28, 2017 (JP) .............................. JP2017-062306

(51) Int. Cl.
*H04N 5/355* (2011.01)
*H04N 5/232* (2006.01)
(Continued)

(52) U.S. Cl.
CPC ......... *H04N 5/355* (2013.01); *A61B 1/00009* (2013.01); *H04N 5/23229* (2013.01);
(Continued)

(58) Field of Classification Search
CPC ... A61B 1/00009; A61B 1/0684; A61B 1/043; A61B 1/00188; A61B 1/05;
(Continued)

(56) References Cited

U.S. PATENT DOCUMENTS 6,747,694 B1 * 6/2004 Nishikawa ............. H04N 5/235
348/223.1
7,245,322 B2 * 7/2007 Oda ....................... H04N 3/155
348/243
(Continued)

FOREIGN PATENT DOCUMENTS

JP 2004-222154 A 8/2004
JP 2004-222184 A 8/2004
(Continued)

OTHER PUBLICATIONS

International Search Report and Written Opinion of PCT Application No. PCT/JP2018/010162, dated May 22, 2018, 08 pages of ISRWO.

*Primary Examiner* — Timothy J Henn
(74) *Attorney, Agent, or Firm* — Chip Law Group

(57) ABSTRACT

The present technology relates to an image processing apparatus, an image processing method, and an electronic apparatus that make it possible to suppress, where a pixel signal of a large pixel and a pixel signal of a small pixel are composed to generate a WD image, degradation of image quality of the WD image. An image processing apparatus includes a first acquisition unit that acquires a first pixel signal output from a first pixel, a second acquisition unit that acquires a second pixel signal output from a second pixel having a size smaller than that of the first pixel, a temperature detection unit that detects temperature, a composition gain determination unit that determines a composition gain corresponding to the detected temperature, and a composi-
(Continued)

tion unit that composes the first pixel signal and the second pixel signal multiplied by the composition gain.

10 Claims, 10 Drawing Sheets

(51) Int. Cl.
 *H04N 5/243* (2006.01)
 *H04N 5/225* (2006.01)
 *A61B 1/00* (2006.01)
(52) U.S. Cl.
 CPC ......... *H04N 5/243* (2013.01); *H04N 5/35563* (2013.01); *H04N 2005/2255* (2013.01)
(58) Field of Classification Search
 CPC .... A61B 1/00006; A61B 1/045; H04N 5/355; H04N 5/23229; H04N 2005/2255; H04N 5/23296; H04N 9/045; H04N 5/232; H04N 5/243; H04N 5/2353; H04N 5/35563
 See application file for complete search history.

(56) References Cited

U.S. PATENT DOCUMENTS

| | | | | |
|---|---|---|---|---|
| 7,382,403 B2* | 6/2008 | Sakamoto | ............. | H04N 5/235 348/229.1 |
| 7,598,986 B2* | 10/2009 | Suemoto | ................ | H04N 9/735 348/222.1 |
| 7,649,554 B2* | 1/2010 | Suzuki | ................... | H04N 5/235 348/239 |
| 7,791,665 B2* | 9/2010 | Kawai | .................... | H04N 5/235 348/315 |
| 8,908,068 B2* | 12/2014 | Yagyu | .................. | H04N 5/2621 348/272 |
| 9,628,725 B2* | 4/2017 | Roh | ................. | H04N 5/35554 |
| 9,635,333 B2* | 4/2017 | Cho | ........................ | G06T 5/007 |
| 9,690,997 B2* | 6/2017 | Murao | ............... | G06K 9/00825 |
| 2004/0051790 A1* | 3/2004 | Tamaru | .................. | H04N 5/235 348/223.1 |
| 2004/0051796 A1* | 3/2004 | Kelly | .................. | H04N 5/3651 348/243 |
| 2004/0145672 A1 | 7/2004 | Sugimoto | | |
| 2007/0065038 A1* | 3/2007 | Maschauer | .......... | H04N 5/2355 382/274 |
| 2007/0223059 A1* | 9/2007 | Oishi | .................. | H04N 1/0408 358/482 |
| 2009/0046180 A1 | 2/2009 | Shibano et al. | | |
| 2010/0231748 A1 | 9/2010 | Takeda | | |

FOREIGN PATENT DOCUMENTS

| | | |
|---|---|---|
| JP | 2007-214932 A | 8/2007 |
| JP | 2012-165479 A | 8/2012 |

* cited by examiner

IMAGE PROCESSING APPARATUS, IMAGE PROCESSING METHOD, AND ELECTRONIC APPARATUS

CROSS REFERENCE TO RELATED APPLICATIONS

This application is a U.S. National Phase of International Patent Application No. PCT/JP2018/010162 filed on Mar. 15, 2018, which claims priority benefit of Japanese Patent Application No. JP 2017-062306 filed in the Japan Patent Office on Mar. 28, 2017. Each of the above-referenced applications is hereby incorporated herein by reference in its entirety.

TECHNICAL FIELD

The present technology relates to an image processing apparatus, an image processing method, and an electronic apparatus, and particularly to an image processing apparatus, an image processing method, and an electronic apparatus that compose pixel signals output from pixels having different light reception sensitivities to generate a WD (wide dynamic range) image.

BACKGROUND ART

As a method of generating a WD image, a method of providing a first pixel and a second pixel having different sensitivities on a pixel array such as a CMOS (complementary metal-oxide semiconductor) image sensor and composing outputs of the pixels, i.e., a first image and a second image has been known.

Here, examples of providing pixels having different sensitivities include a method of providing a pixel having a long exposure time (hereinafter, referred to as long accumulation pixel) and a pixel having a short exposure time (hereinafter, referred to as short accumulation pixel) and a method of providing a pixel that includes a photoelectric conversion unit such as a PD (photodiode) having a large size (hereinafter, referred to as large pixel) and a pixel that includes a photoelectric conversion unit such as a PD having a small size (hereinafter, referred to as small pixel) (see, for example, Patent Literature 1).

CITATION LIST

Patent Literature

Patent Literature 1: Japanese Patent Application Laid-open No. 2004-222154

DISCLOSURE OF INVENTION

Technical Problem

In the method of providing the long accumulation pixel and the short accumulation pixel, both the pixel have the same structure, and various characteristics that can depend on the temperature of both pixels are common. Therefore, it is not necessary to consider temperature also when composing pixel signals of both pixels.

Meanwhile, in the method of providing the large pixel and the small pixel, both the pixels have different structures. That is, the size of the photoelectric conversion unit such as a PD differs between both pixels, and various characteristics that change depending on temperature of both pixels differ.

Examples of the various characteristics that change depending on temperature include sensitivity characteristics, saturation charge amount Qs, conversion efficiency, white spot generation characteristics, and black spot generation characteristics. Hereinafter, these are collectively referred to as temperature dependent characteristics.

Therefore, in the case where a pixel signal of a large pixel and a pixel signal of a small pixel are composed, if the above-mentioned temperature dependent characteristics are not considered, a step occurs at the junction of the pixel signal of the large pixel and the pixel signal of the small pixel depending on temperature or the change in pixel signal with respect to the change in luminance of an object cannot maintain the linearity in some cases. In such a case, degradation of image quality such as generation of false color on the generated WD image occurs.

The present technology has been made in view of the above-mentioned circumstances and it is an object thereof to suppress, where a pixel signal of a large pixel and a pixel signal of a small pixel are composed to generate a WD image, degradation of image quality of the WD image.

Solution to Problem

An image processing apparatus according to a first aspect of the present technology includes: a first acquisition unit that acquires a first pixel signal output from a first pixel; a second acquisition unit that acquires a second pixel signal output from a second pixel having a size smaller than that of the first pixel; a temperature detection unit that detects temperature; a composition gain determination unit that determines a composition gain corresponding to the detected temperature; and a composition unit that composes the first pixel signal and the second pixel signal multiplied by the composition gain.

An image processing method according to a first aspect of the present technology includes: performing, by the image processing apparatus, a first acquisition step of acquiring a first pixel signal output from a first pixel; a second acquisition step of acquiring a second pixel signal output from a second pixel having a size smaller than that of the first pixel; a temperature detection step of detecting temperature; a composition gain determination step of determining a composition gain corresponding to the detected temperature; and a composition step of composing the first pixel signal and the second pixel signal multiplied by the composition gain.

An electronic apparatus according to a second aspect of the present technology is an electronic apparatus on which a solid-state image sensor is mounted, the solid-state image sensor including: a pixel unit, a plurality of first pixels and a plurality of second pixels being arranged in the pixel unit, each of the plurality of second pixels having a size smaller than that of each of the plurality of first pixels; a first acquisition unit that acquires a first pixel signal output from the first pixel; a second acquisition unit that acquires a second pixel signal output from the second pixel; a temperature detection unit that detects temperature; a composition gain determination unit that determines a composition gain corresponding to the detected temperature; and a composition unit that composes the first pixel signal and the second pixel signal multiplied by the composition gain.

In the first and second aspects of the present technology, a first pixel signal output from a first pixel is acquired; a second pixel signal output from a second pixel having a size smaller than that of the first pixel is acquired; temperature is detected; a composition gain corresponding to the detected temperature is determined; and the first pixel signal and the second pixel signal multiplied by the composition gain are composed.

Advantageous Effects of Invention

In accordance with the first aspect of the present technology, it is possible to suppress degradation of image quality of a WD image obtained by composing a pixel signal of a large pixel and a pixel signal of a small pixel.

MODE(S) FOR CARRYING OUT THE INVENTION

Hereinafter, the best mode for carrying out the present technology (hereinafter, referred to as embodiment) will be described in detail with reference to the drawings.

<Configuration Example of Image Processing Apparatus according to Embodiment of Present Technology>

Figure 1:
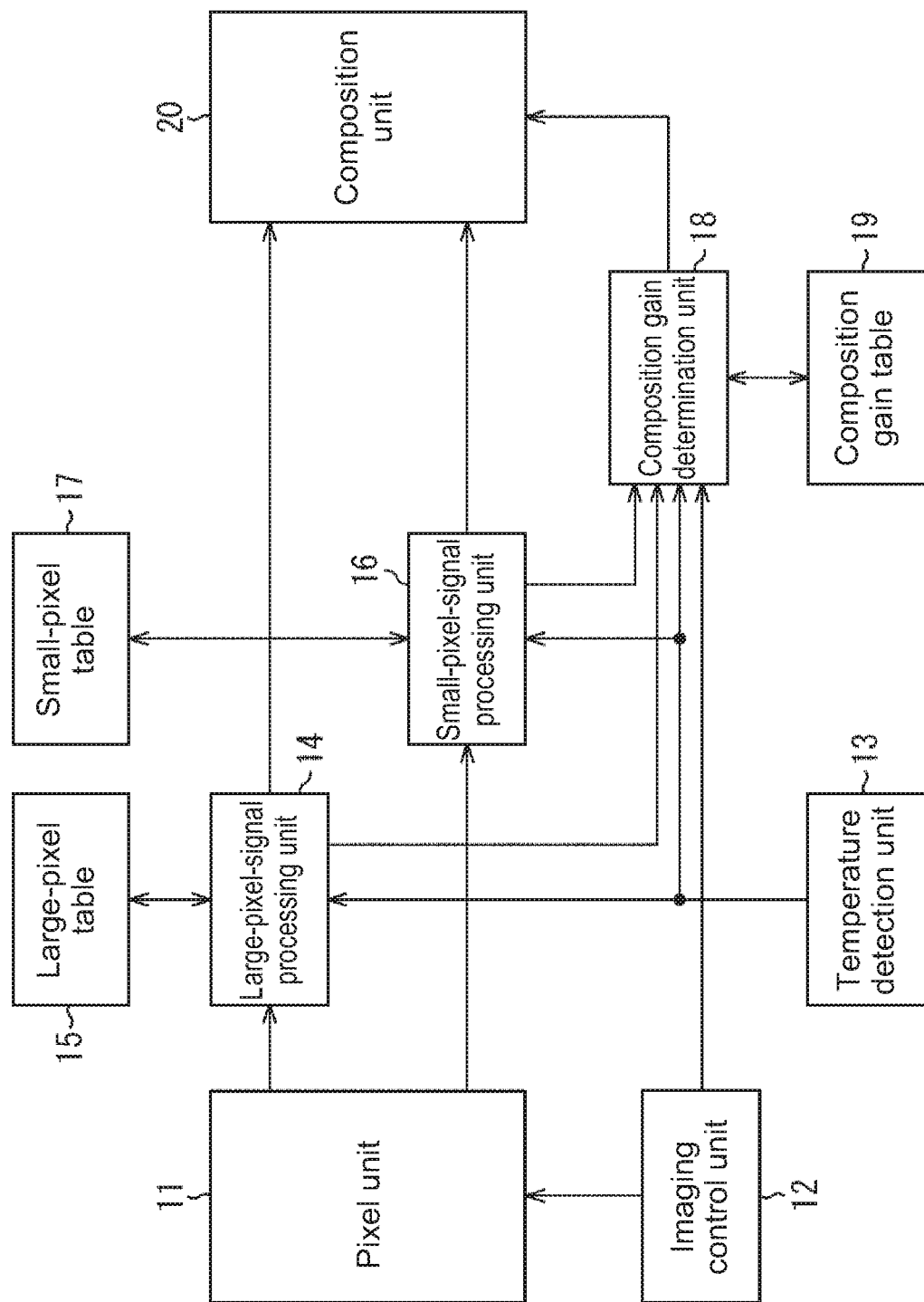
FIG. 1 is a block diagram showing a configuration example of an image processing apparatus to which the present technology is applied.

FIG. 1 is a block diagram showing a configuration example of an image processing apparatus according to an embodiment of the present technology.

The image processing apparatus includes a pixel unit 11, an imaging control unit 12, a temperature detection unit 13, a large-pixel-signal processing unit 14, a large-pixel table 15, a small-pixel-signal processing unit 16, a small-pixel table 17, a composition gain determination unit 18, a composition gain table 19, and a composition unit 20.

The pixel unit 11 includes a solid-state image sensor such as a CMOS image sensor in which a large pixel and a small pixel having different light reception sensitivities are arranged in accordance with a predetermined rule. Note that the large pixel and the small pixel each include any of color filters of R (red), G (green), and B (blue) or a filter for acquiring a wavelength band other than visible light, and generates a pixel signal including a color component of R, G, or B or a wavelength band other than visible light. The pixel unit 11 outputs a pixel signal of the large pixel to the large-pixel-signal processing unit 14, and a pixel signal of the small pixel to the small-pixel-signal processing unit 16.

Hereinafter, the pixel signal of the large pixel will be referred to as large-pixel signal, and the pixel signal of the small pixel will be referred to as small-pixel signal.

The imaging control unit 12 controls the operation of the pixel unit 11. In particular, the imaging control unit 12 controls the exposure time of the large pixel of the pixel unit 11 and the exposure time of the small pixel of the pixel unit 11, and notifies the composition gain determination unit 18 of each of the exposure times.

The temperature detection unit 13 detects temperature of the pixel unit 11, and notifies the large-pixel-signal processing unit 14, the small-pixel-signal processing unit 16, and the composition gain determination unit 18 of the detected temperature.

The large-pixel-signal processing unit 14 performs predetermined signal processing corresponding to temperature on the large-pixel signal input from the pixel unit 11, and outputs, to the composition unit 20, the large-pixel signal on which signal processing has been performed.

For example, the large-pixel-signal processing unit 14 acquires, from the large-pixel table 15, an OB (optical black) clamp value that changes depending on the change in temperature, and performs OB clamp processing on the large-pixel signal. Further, for example, the large-pixel-signal processing unit 14 acquires, from the large-pixel table 15, the minimum gain corresponding to a saturation signal amount Qs that changes depending on the change in temperature, and multiplies the large-pixel signal by the acquired minimum gain.

Further, the large-pixel-signal processing unit 14 notifies the composition gain determination unit 18 of the minimum gain as a multiplication target for the large-pixel signal.

In the large-pixel table 15, various temperature dependent parameters based on 45° C. at which it can be assumed that there is no difference between temperature dependent characteristics of the large pixel and the small pixel are stored as a table in advance. The various temperature dependent parameters are used in signal processing by the large-pixel-signal processing unit 14. Note that instead of the table, the various temperature dependent parameters may be stored as a function of temperature.

The small-pixel-signal processing unit 16 performs predetermined signal processing corresponding to temperature on the small-pixel signal input from the pixel unit 11, and outputs, to the composition unit 20, the large-pixel signal on which the signal processing has been performed.

For example, the small-pixel-signal processing unit 16 acquires, from the small-pixel table 17, an OB clamp value that changes depending on the change in temperature, and perform OB clamp processing on the small-pixel signal. Further, for example, the small-pixel-signal processing unit 16 acquires, from the small-pixel table 17, the minimum gain corresponding to the saturation signal amount Qs that changes depending on the change in temperature, and multiplies the small-pixel signal by the acquired minimum gain.

Further, the small-pixel-signal processing unit 16 notifies the composition gain determination unit 18 of the minimum gain as a multiplication target for the small-pixel signal.

In the small-pixel table 17, various temperature dependent parameters based on 45° C. at which it can be assumed that there is no difference between temperature dependent characteristics of the large pixel and the small pixel are stored as a table in advance. The various temperature dependent parameters are used in signal processing by the small-pixel-signal processing unit 16. Note that instead of the table, the various temperature dependent parameters may be stored as a function of temperature.

The composition gain determination unit 18 acquires, from the composition gain table 19, a temperature dependent correction amount different for each of color components of R, G, and B corresponding to temperature notified from the temperature detection unit 13. Further, the composition gain determination unit 18 determines the composition gain for each color component by applying the temperature dependent correction amount, the exposure time of each of the large pixel and the small pixel notified from the imaging control unit 12, the minimum gain notified from the large-pixel-signal processing unit 14, the minimum gain notified from the small-pixel-signal processing unit 16, and the composition gain at 45° C. held in advance to the following formula (1), and notifies the composition unit 20 of the determined composition gain.

Composition gain=composition gain at 45° C.×(exposure time of large pixel/exposure time of small pixel)×(minimum gain of large pixel/minimum gain of large pixel)×temperature dependent correction amount (1)

In the composition gain table 19, a temperature dependent correction amount for which an appropriate value corresponding to temperature has been obtained is stored in advance as a table.

Figure 2:
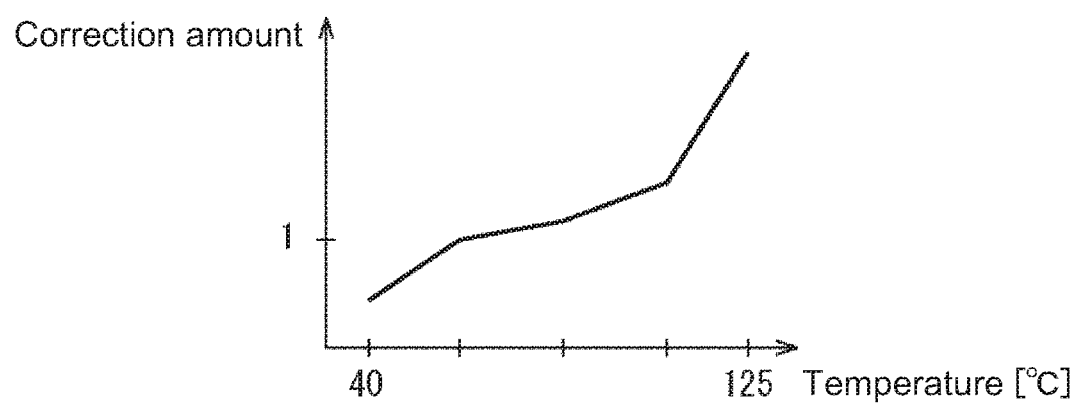
FIG. 2 is a diagram showing an example of a temperature dependent correction amount corresponding to temperature.

FIG. 2 shows an example of the temperature dependent correction amount corresponding to temperature. The horizontal axis of the figure indicates temperature [° C.], and the vertical axis indicates the correction amount. In the figure, the correction amount at 45° C. that is a reference value is one, and the correction amount is set to gradually increase as the temperature rises. On the contrary, the correction amount is set to be reduced in the case where the temperature falls below 45° C. that is a reference value.

Note that in the case where the exposure time of the large pixel, the exposure time of the small pixel, the minimum gain of the large pixel, and the minimum gain of the large pixel are each a fixed value or a variable that depends on temperature, instead of causing the composition gain table 19 to hold the temperature dependent correction amount corresponding to temperature, the composition gain table 19 may be caused to hold a composition gain corresponding to temperature calculated in advance.

The composition unit 20 composes the large-pixel signal on which predetermined signal processing has been performed and the result obtained by multiplying the small-pixel signal on which predetermined signal processing has been performed by the composition gain to generate a WD image. For example, the WD image is generated by adopting the large-pixel signal in the case where luminance of an object is low to lower than the luminance where the large-pixel signal is saturated, and adopting the small-pixel signal multiplied by the composition gain in the case of luminance equal to or higher than the luminance where the large pixel is saturated. Further, for example, a composition rate of one or less corresponding to luminance is set, and the result obtained by multiplying the large-pixel signal on which predetermined signal processing has been performed by the addition rate, and the result obtained by multiplying the small-pixel signal on which predetermined signal processing has been performed by the composition gain (1-composition rate) are added to generate a WD image.

<WD Image Generation Processing by Image Processing Apparatus according to Embodiment of Present Technology>

Figure 3:
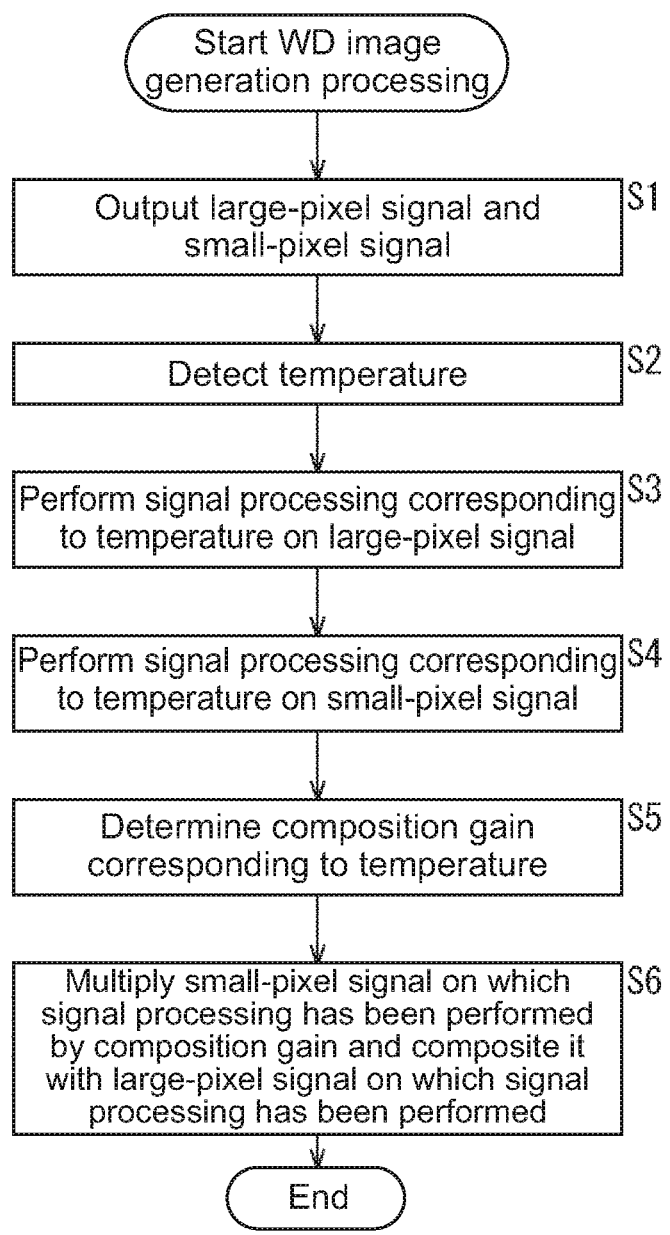
FIG. 3 is a flowchart describing WD image generation processing by an image processing apparatus to which the present technology is applied.

FIG. 3 is a flowchart describing WD image generation processing by the image processing apparatus.

In Step S1, the pixel unit 11 performs imaging in accordance with control from the imaging control unit 12, and outputs the large-pixel signal and the small-pixel signal. The large-pixel signal is acquired by the large-pixel-signal processing unit 14, and the small-pixel signal is acquired by the small-pixel-signal processing unit 16. In Step S2, the temperature detection unit 13 detects the temperature of the pixel unit 11, and notifies the large-pixel-signal processing unit 14, the small-pixel-signal processing unit 16, and the composition gain determination unit 18 of the detected temperature.

In Step S3, the large-pixel-signal processing unit 14 performs predetermined signal processing corresponding to temperature on the large-pixel signal input from the pixel unit 11, and outputs, to the composition unit 20, the large-pixel signal on which signal processing has been performed. In Step S4, the small-pixel-signal processing unit 16 performs predetermined signal processing corresponding to temperature on the small-pixel signal input from the pixel unit 11, and outputs, to the composition unit 20, the small-pixel signal on which signal processing has been performed.

In Step S5, the composition gain determination unit 18 acquires, from the composition gain table 19, the temperature dependent correction amount corresponding to temperature notified from the temperature detection unit 13. Further, the composition gain determination unit 18 determines the composition gain by applying the temperature dependent correction amount, the exposure time of each of the large pixel and the small pixel notified from the imaging control unit 12, the minimum gain notified from the large-pixel-signal processing unit 14, the minimum gain notified from the small-pixel-signal processing unit 16, and the composition gain at 60° C. held in advance to the formula (1), and notifies the composition unit 20 of the determined composition gain.

In Step S6, the composition unit 20 composes the large-pixel signal on which predetermined signal processing has been performed and the result obtained by multiplying the small-pixel signal on which predetermined signal processing has been performed by the composition gain to generate a WD image. In this way, the WD image generation processing is finished.

<Effects of WD Image Generation Processing by Image Processing Apparatus according to Embodiment of Present Technology>

The effects of the above-mentioned WD image generation processing will be described.

Figure 4:
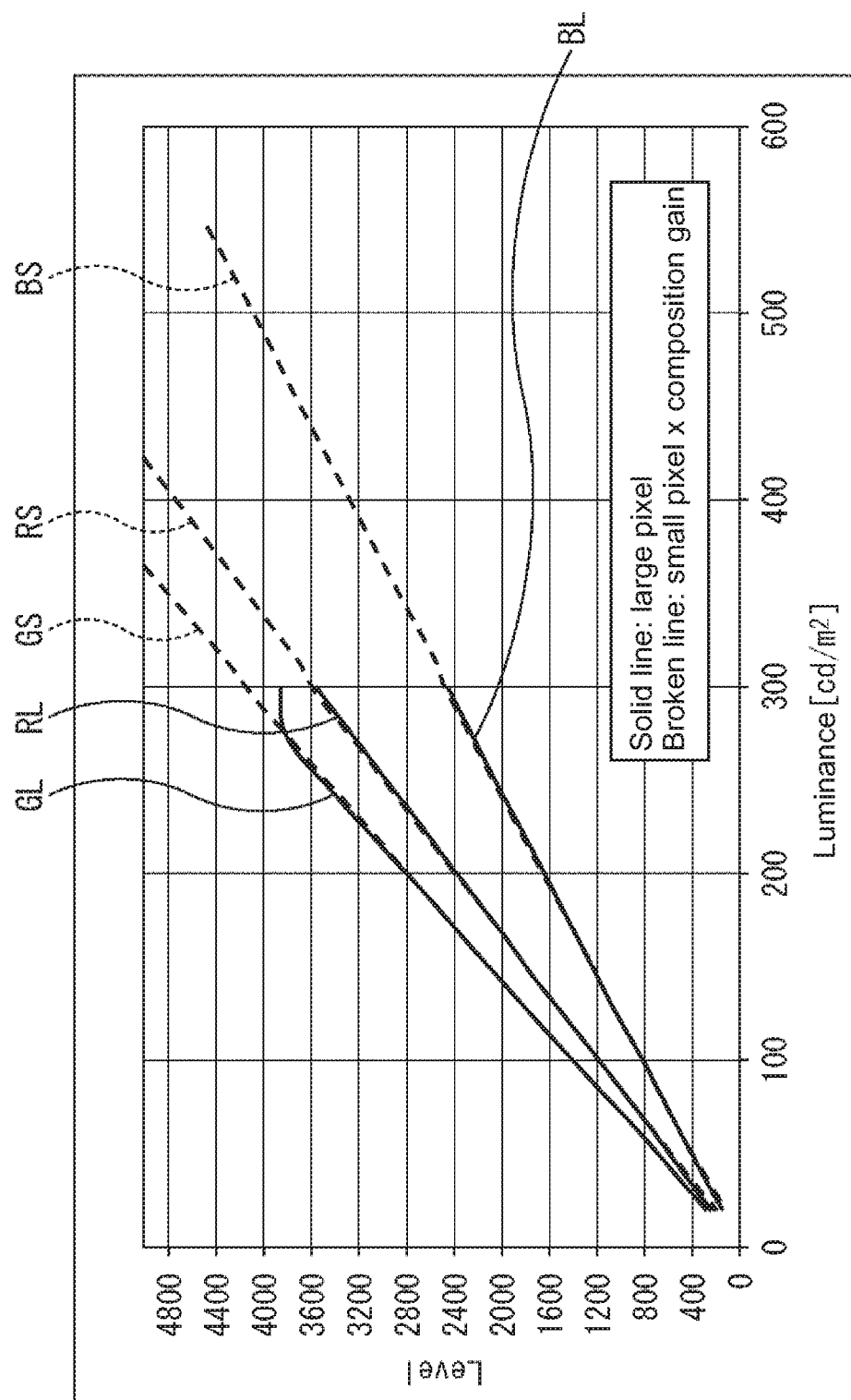
FIG. 4 is a diagram showing the results of an existing composition method at 60° C.

FIG. 4 shows the change in luminance of an object and the change in level of the pixel signal in the case where the large-pixel signal and the small-pixel signal are composed at 45° C. that is a reference value of temperature at which it can be assumed that there is no difference between temperature dependent characteristics of the large pixel and the small pixel by an existing method that does not consider temperature dependent characteristics of the large pixel and the small pixel. In the figure, solid lines RL, GL, and BL respectively indicate R, G, and B components of the large-pixel signal, and broken lines RS, GS, and BS respectively indicate R, G, and B components of the small-pixel signal multiplied by the composition gain.

Note that also in the case where the large-pixel signal and the small-pixel signal are composed at 45° C. by the WD image generation processing, results similar to those in FIG. 4 are obtained.

That is, the solid line RL and the broken line RS, the solid line GL and the broken line GS, and the solid line BL and the broken line BS are connected without any step, and the pixel signal level with respect to the change in luminance is capable of maintaining linearity.

Figure 5:
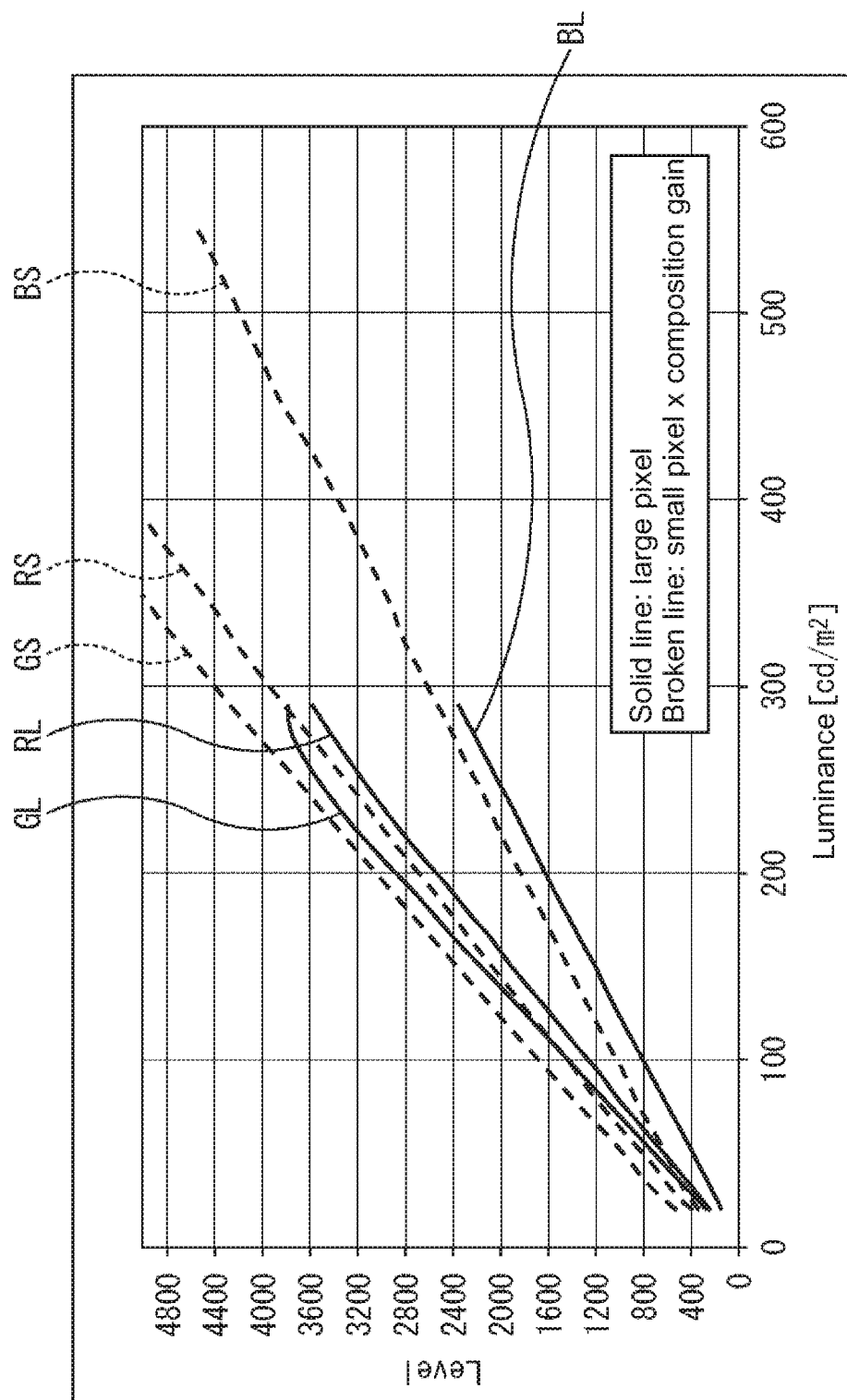
FIG. 5 is a diagram showing the results of an existing composition method at 105° C.

FIG. 5 shows the change in luminance of an object and the change in level of the pixel signal in the case where the large-pixel signal and the small-pixel signal are composed at 105° C., which greatly exceeds the reference value 45° C., by an existing method that does not consider temperature dependent characteristics of the large pixel and the small pixel. In the figure, solid lines RL, GL, and BL respectively solid lines RL, GL, and BL respectively indicate R, G, and B components of the large-pixel signal, and broken lines RS, GS, and BS respectively indicate R, G, and B components of the small-pixel signal multiplied by the composition gain.

In the case of 105° C., since a difference occurs between temperature dependent characteristics of the large pixel and the small pixel, the solid line RL and the broken line RS, the solid line GL and the broken line GS, and the solid line BL and the broken line BS are not connected well as shown in FIG. 5, and degradation of image quality such as generation of false color near the junction occurs.

Figure 6:
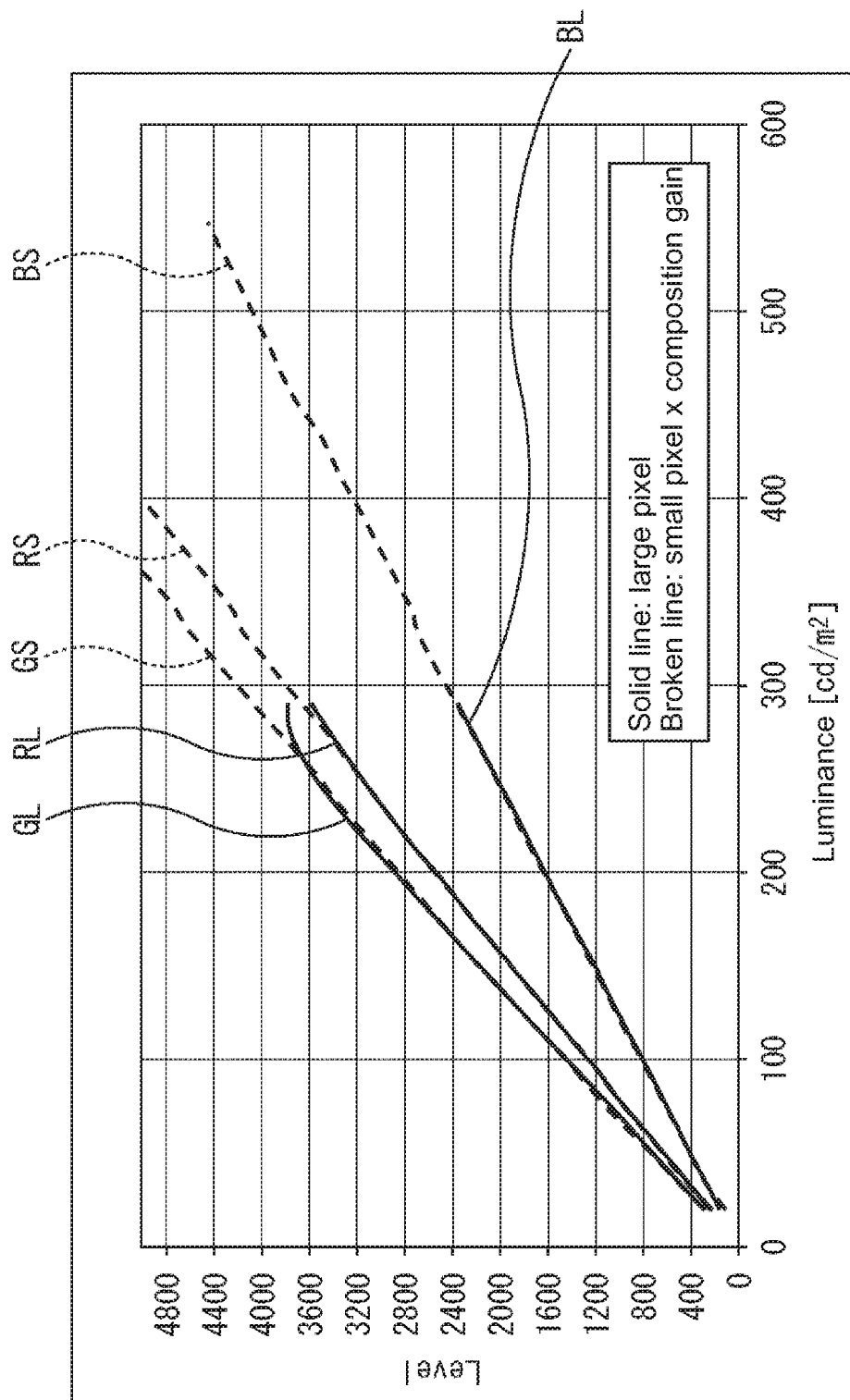
FIG. 6 is a diagram showing the results of the WD image generation processing at 105° C.

FIG. 6 shows the change in luminance of an object and the change in level of the pixel signal in the case where the large-pixel signal and the small-pixel signal are composed at 105° C., which greatly exceeds the reference value 45° C., by the above-mentioned WD composition processing. In the figure, solid lines RL, GL, and BL respectively solid lines RL, GL, and BL respectively indicate R, G, and B components of the large-pixel signal, and broken lines RS, GS, and BS respectively indicate R, G, and B components of the small-pixel signal multiplied by the composition gain.

In the case of 105° C., although a difference occurs between temperature dependent characteristics of the large pixel and the small pixel, since the composition gain as a multiplication target of the small-pixel signal is determined corresponding to temperature, as shown in FIG. 6, the solid line RL and the broken line RS, the solid line GL and the broken line GS, and the solid line BL and the broken line BS are smoothly connected as compared with FIG. 5, and the pixel signal level with respect to the change in luminance is capable of maintaining linearity. Therefore, it is possible to suppress degradation of image quality such as generation of false color near the junction.

Modified Example

In the above description, the pixel unit 11 of the image processing apparatus shown in FIG. 1 has included a solid-state image sensor such as a CMOS image sensor. However, the solid-state image sensor may include components other than the pixel unit 11 in FIG. 1. That is, the solid-state image sensor may include all the components shown in FIG. 1.

<Example of Application to Endoscopic Surgery System>

The technology according to the present disclosure (present technology) is applicable to various products. For example, the technology according to the present disclosure may be applied to an endoscopic surgery system.

Figure 7:
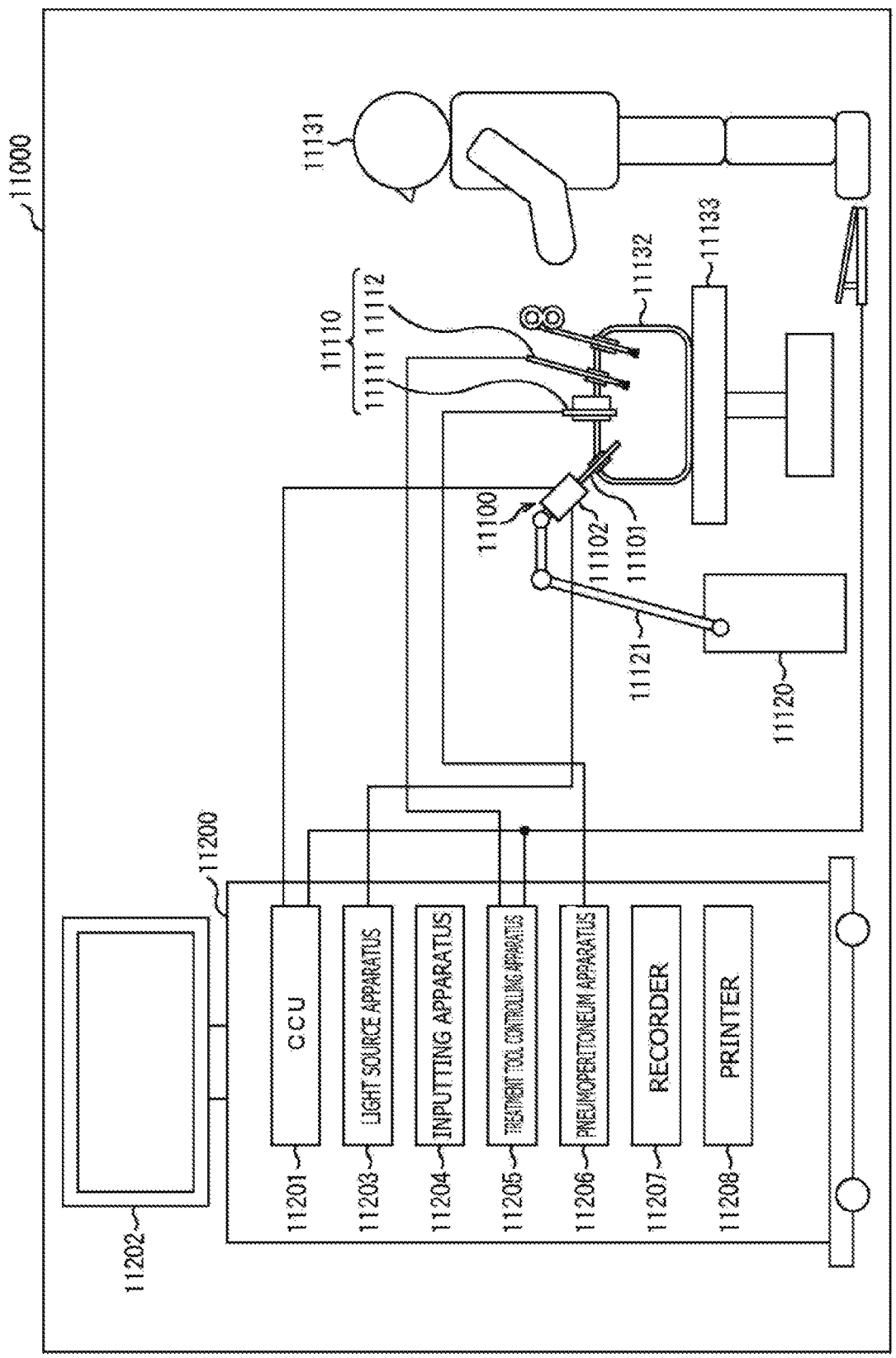
FIG. 7 is a view depicting an example of a schematic configuration of an endoscopic surgery system.

FIG. 7 is a view depicting an example of a schematic configuration of an endoscopic surgery system to which the technology according to an embodiment of the present disclosure (present technology) can be applied.

In FIG. 7, a state is illustrated in which a surgeon (medical doctor) 11131 is using an endoscopic surgery system 11000 to perform surgery for a patient 11132 on a patient bed 11133. As depicted, the endoscopic surgery system 11000 includes an endoscope 11100, other surgical tools 11110 such as a pneumoperitoneum tube 11111 and an energy treatment tool 11112, a supporting arm apparatus 11120 which supports the endoscope 11100 thereon, and a cart 11200 on which various apparatus for endoscopic surgery are mounted.

The endoscope 11100 includes a lens barrel 11101 having a region of a predetermined length from a distal end thereof to be inserted into a body lumen of the patient 11132, and a camera head 11102 connected to a proximal end of the lens barrel 11101. In the example depicted, the endoscope 11100 is depicted which includes as a hard mirror having the lens barrel 11101 of the hard type. However, the endoscope 11100 may otherwise be included as a soft mirror having the lens barrel 11101 of the soft type.

The lens barrel 11101 has, at a distal end thereof, an opening in which an objective lens is fitted. A light source apparatus 11203 is connected to the endoscope 11100 such that light generated by the light source apparatus 11203 is introduced to a distal end of the lens barrel 11101 by a light guide extending in the inside of the lens barrel 11101 and is irradiated toward an observation target in a body lumen of the patient 11132 through the objective lens. It is to be noted that the endoscope 11100 may be a direct view mirror or may be a perspective view mirror or a side view mirror.

An optical system and an image pickup element are provided in the inside of the camera head 11102 such that reflected light (observation light) from the observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 11201.

The CCU 11201 includes a central processing unit (CPU), a graphics processing unit (GPU) or the like and integrally controls operation of the endoscope 11100 and a display apparatus 11202. Further, the CCU 11201 receives an image signal from the camera head 11102 and performs, for the image signal, various image processes for displaying an image based on the image signal such as, for example, a development process (demosaic process).

The display apparatus 11202 displays thereon an image based on an image signal, for which the image processes have been performed by the CCU 11201, under the control of the CCU 11201.

The light source apparatus 11203 includes a light source such as, for example, a light emitting diode (LED) and supplies irradiation light upon imaging of a surgical region to the endoscope 11100.

An inputting apparatus 11204 is an input interface for the endoscopic surgery system 11000. A user can perform inputting of various kinds of information or instruction inputting to the endoscopic surgery system 11000 through the inputting apparatus 11204. For example, the user would input an instruction or a like to change an image pickup condition (type of irradiation light, magnification, focal distance or the like) by the endoscope 11100.

A treatment tool controlling apparatus 11205 controls driving of the energy treatment tool 11112 for cautery or incision of a tissue, sealing of a blood vessel or the like. A pneumoperitoneum apparatus 11206 feeds gas into a body lumen of the patient 11132 through the pneumoperitoneum tube 11111 to inflate the body lumen in order to secure the field of view of the endoscope 11100 and secure the working space for the surgeon. A recorder 11207 is an apparatus capable of recording various kinds of information relating to surgery. A printer 11208 is an apparatus capable of printing various kinds of information relating to surgery in various forms such as a text, an image or a graph.

It is to be noted that the light source apparatus 11203 which supplies irradiation light when a surgical region is to be imaged to the endoscope 11100 may include a white light source which includes, for example, an LED, a laser light source or a combination of them. Where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 11203. Further, in this case, if laser beams from the respective RGB laser light sources are irradiated time-divisionally on an observation target and driving of the image pickup elements of the camera head 11102 are controlled in synchronism with the irradiation timings. Then images individually corresponding to the R, G and B colors can be also picked up time-divisionally. According to this method, a color image can be obtained even if color filters are not provided for the image pickup element.

Further, the light source apparatus 11203 may be controlled such that the intensity of light to be outputted is changed for each predetermined time. By controlling driving of the image pickup element of the camera head 11102 in synchronism with the timing of the change of the intensity of light to acquire images time-divisionally and synthesizing the images, an image of a high dynamic range free from underexposed blocked up shadows and overexposed highlights can be created.

Further, the light source apparatus 11203 may be configured to supply light of a predetermined wavelength band ready for special light observation. In special light observation, for example, by utilizing the wavelength dependency of absorption of light in a body tissue to irradiate light of a narrow band in comparison with irradiation light upon ordinary observation (namely, white light), narrow band observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 11203 can be configured to supply such narrow-band light and/or excitation light suitable for special light observation as described above.

Figure 8:
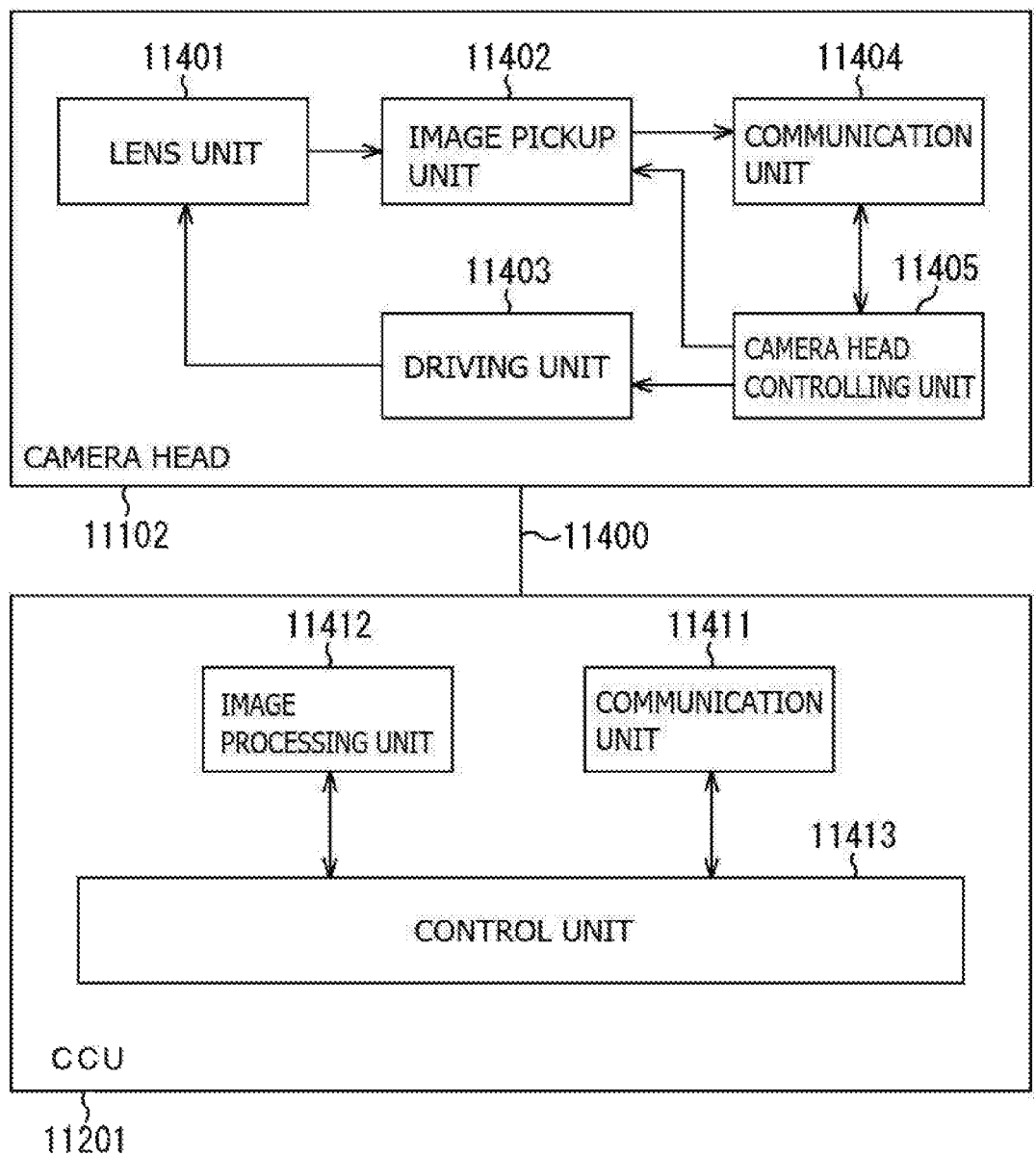
FIG. 8 is a block diagram depicting an example of a functional configuration of a camera head and a camera control unit (CCU).

FIG. 8 is a block diagram depicting an example of a functional configuration of the camera head 11102 and the CCU 11201 depicted in FIG. 7.

The camera head 11102 includes a lens unit 11401, an image pickup unit 11402, a driving unit 11403, a communication unit 11404 and a camera head controlling unit 11405. The CCU 11201 includes a communication unit 11411, an image processing unit 11412 and a control unit 11413. The camera head 11102 and the CCU 11201 are connected for communication to each other by a transmission cable 11400.

The lens unit 11401 is an optical system, provided at a connecting location to the lens barrel 11101. Observation light taken in from a distal end of the lens barrel 11101 is guided to the camera head 11102 and introduced into the lens unit 11401. The lens unit 11401 includes a combination of a plurality of lenses including a zoom lens and a focusing lens.

The image pickup unit 11402 is configured as an image pickup element. The number of image pickup elements which is included by the image pickup unit 11402 may be one (single-plate type) or a plural number (multi-plate type). Where the image pickup unit 11402 is configured as that of the multi-plate type, for example, image signals corresponding to respective R, G and B are generated by the image pickup elements, and the image signals may be synthesized to obtain a color image. The image pickup unit 11402 may also be configured so as to have a pair of image pickup elements for acquiring respective image signals for the right eye and the left eye ready for three dimensional (3D) display. If 3D display is performed, then the depth of a living body tissue in a surgical region can be comprehended more accurately by the surgeon 11131. It is to be noted that, where the image pickup unit 11402 is configured as that of stereoscopic type, a plurality of systems of lens units 11401 are provided corresponding to the individual image pickup elements.

Further, the image pickup unit 11402 may not necessarily be provided on the camera head 11102. For example, the image pickup unit 11402 may be provided immediately behind the objective lens in the inside of the lens barrel 11101.

The driving unit 11403 includes an actuator and moves the zoom lens and the focusing lens of the lens unit 11401 by a predetermined distance along an optical axis under the control of the camera head controlling unit 11405. Consequently, the magnification and the focal point of a picked up image by the image pickup unit 11402 can be adjusted suitably.

The communication unit 11404 includes a communication apparatus for transmitting and receiving various kinds of information to and from the CCU 11201. The communication unit 11404 transmits an image signal acquired from the image pickup unit 11402 as RAW data to the CCU 11201 through the transmission cable 11400.

In addition, the communication unit 11404 receives a control signal for controlling driving of the camera head 11102 from the CCU 11201 and supplies the control signal to the camera head controlling unit 11405. The control signal includes information relating to image pickup conditions such as, for example, information that a frame rate of a picked up image is designated, information that an exposure value upon image picking up is designated and/or information that a magnification and a focal point of a picked up image are designated.

It is to be noted that the image pickup conditions such as the frame rate, exposure value, magnification or focal point may be designated by the user or may be set automatically by the control unit 11413 of the CCU 11201 on the basis of an acquired image signal. In the latter case, an auto exposure (AE) function, an auto focus (AF) function and an auto white balance (AWB) function are incorporated in the endoscope 11100.

The camera head controlling unit 11405 controls driving of the camera head 11102 on the basis of a control signal from the CCU 11201 received through the communication unit 11404.

The communication unit 11411 includes a communication apparatus for transmitting and receiving various kinds of information to and from the camera head 11102. The communication unit 11411 receives an image signal transmitted thereto from the camera head 11102 through the transmission cable 11400.

Further, the communication unit 11411 transmits a control signal for controlling driving of the camera head 11102 to the camera head 11102. The image signal and the control signal can be transmitted by electrical communication, optical communication or the like.

The image processing unit 11412 performs various image processes for an image signal in the form of RAW data transmitted thereto from the camera head 11102.

The control unit 11413 performs various kinds of control relating to image picking up of a surgical region or the like by the endoscope 11100 and display of a picked up image obtained by image picking up of the surgical region or the like. For example, the control unit 11413 creates a control signal for controlling driving of the camera head 11102.

Further, the control unit 11413 controls, on the basis of an image signal for which image processes have been performed by the image processing unit 11412, the display apparatus 11202 to display a picked up image in which the surgical region or the like is imaged. Thereupon, the control unit 11413 may recognize various objects in the picked up image using various image recognition technologies. For example, the control unit 11413 can recognize a surgical tool such as forceps, a particular living body region, bleeding, mist when the energy treatment tool 11112 is used and so forth by detecting the shape, color and so forth of edges of objects included in a picked up image. The control unit 11413 may cause, when it controls the display apparatus 11202 to display a picked up image, various kinds of surgery supporting information to be displayed in an overlapping manner with an image of the surgical region using a result of the recognition. Where surgery supporting information is displayed in an overlapping manner and presented to the surgeon 11131, the burden on the surgeon 11131 can be reduced and the surgeon 11131 can proceed with the surgery with certainty.

The transmission cable 11400 which connects the camera head 11102 and the CCU 11201 to each other is an electric signal cable ready for communication of an electric signal, an optical fiber ready for optical communication or a composite cable ready for both of electrical and optical communications.

Here, while, in the example depicted, communication is performed by wired communication using the transmission cable 11400, the communication between the camera head 11102 and the CCU 11201 may be performed by wireless communication.

An example of the endoscopic surgery system to which the technology according to the present disclosure can be applied has been described heretofore. The technology according to the present disclosure is applicable to, for example, the endoscope 11100, (the image pickup unit 11402 of) the camera head 11102, and (the image processing unit 11412 of) the CCU 11201 among the above-mentioned configurations.

The technology according to the present disclosure (the present technology) is applicable to various products. For example, the technology according to the present disclosure may be realized as an apparatus mounted on any type of moving objects such as an automobile, an electric car, a hybrid electric vehicle, a motorcycle, a bicycle, personal mobility, an airplane, a drone, a ship, and a robot.

Figure 9:
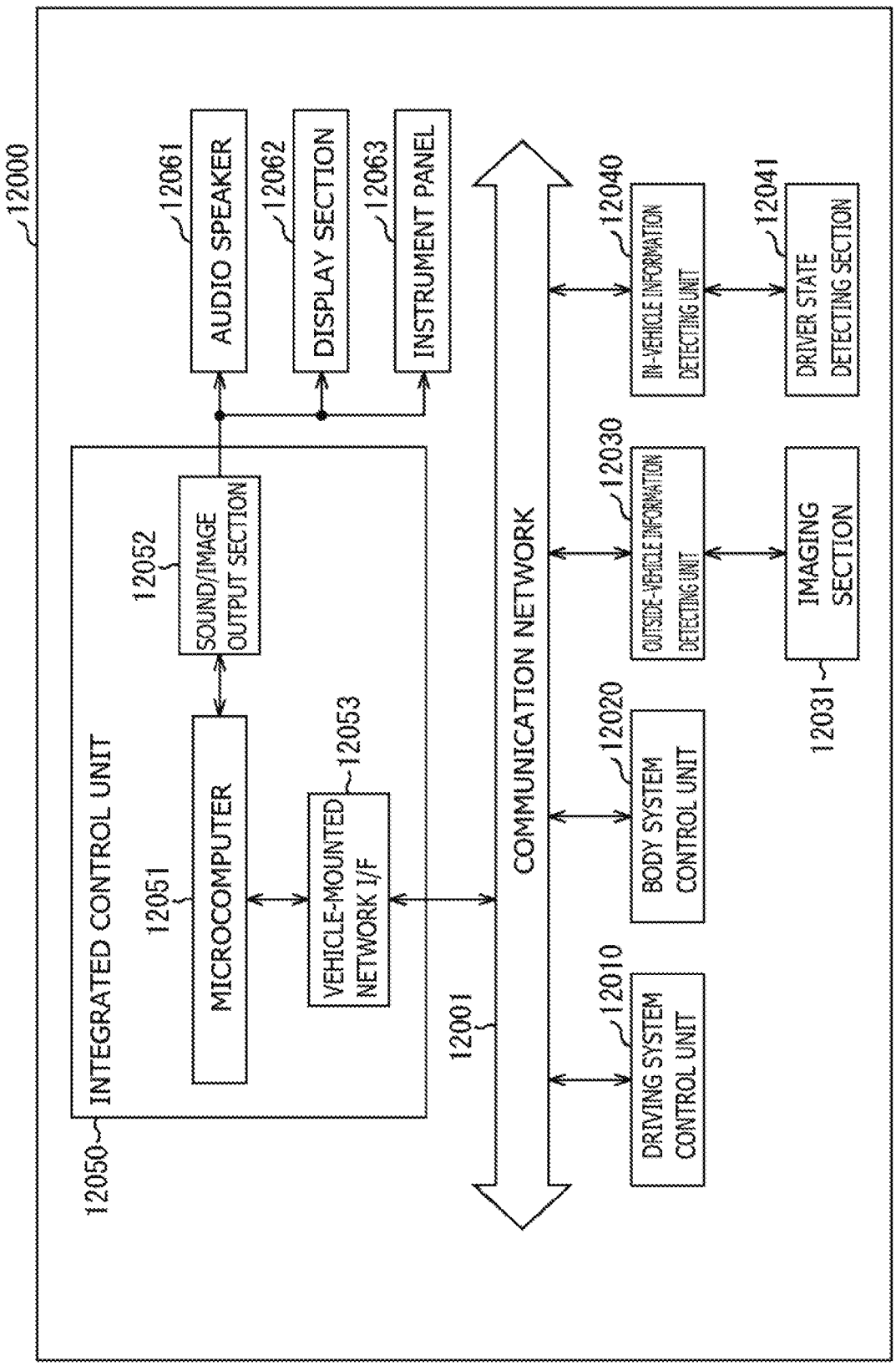
FIG. 9 is a block diagram depicting an example of schematic configuration of a vehicle control system.

FIG. 9 is a block diagram depicting an example of schematic configuration of a vehicle control system as an example of a mobile body control system to which the technology according to an embodiment of the present disclosure can be applied.

The vehicle control system 12000 includes a plurality of electronic control units connected to each other via a communication network 12001. In the example depicted in FIG. 9, the vehicle control system 12000 includes a driving system control unit 12010, a body system control unit 12020, an outside-vehicle information detecting unit 12030, an in-vehicle information detecting unit 12040, and an integrated control unit 12050. In addition, a microcomputer 12051, a sound/image output section 12052, and a vehicle-mounted network interface (I/F) 12053 are illustrated as a functional configuration of the integrated control unit 12050.

The driving system control unit 12010 controls the operation of devices related to the driving system of the vehicle in accordance with various kinds of programs. For example, the driving system control unit 12010 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like.

The body system control unit 12020 controls the operation of various kinds of devices provided to a vehicle body in accordance with various kinds of programs. For example, the body system control unit 12020 functions as a control device for a keyless entry system, a smart key system, a power window device, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 12020. The body system control unit 12020 receives these input radio waves or signals, and controls a door lock device, the power window device, the lamps, or the like of the vehicle.

The outside-vehicle information detecting unit 12030 detects information about the outside of the vehicle including the vehicle control system 12000. For example, the outside-vehicle information detecting unit 12030 is connected with an imaging section 12031. The outside-vehicle information detecting unit 12030 makes the imaging section 12031 image an image of the outside of the vehicle, and receives the imaged image. On the basis of the received image, the outside-vehicle information detecting unit 12030 may perform processing of detecting an object such as a human, a vehicle, an obstacle, a sign, a character on a road surface, or the like, or processing of detecting a distance thereto.

The imaging section 12031 is an optical sensor that receives light, and which outputs an electric signal corresponding to a received light amount of the light. The imaging section 12031 can output the electric signal as an image, or can output the electric signal as information about a measured distance. In addition, the light received by the imaging section 12031 may be visible light, or may be invisible light such as infrared rays or the like.

The in-vehicle information detecting unit 12040 detects information about the inside of the vehicle. The in-vehicle information detecting unit 12040 is, for example, connected with a driver state detecting section 12041 that detects the state of a driver. The driver state detecting section 12041, for example, includes a camera that images the driver. On the basis of detection information input from the driver state detecting section 12041, the in-vehicle information detecting unit 12040 may calculate a degree of fatigue of the driver or a degree of concentration of the driver, or may determine whether the driver is dozing.

The microcomputer 12051 can calculate a control target value for the driving force generating device, the steering mechanism, or the braking device on the basis of the information about the inside or outside of the vehicle which information is obtained by the outside-vehicle information detecting unit 12030 or the in-vehicle information detecting unit 12040, and output a control command to the driving system control unit 12010. For example, the microcomputer 12051 can perform cooperative control intended to implement functions of an advanced driver assistance system (ADAS) which functions include collision avoidance or shock mitigation for the vehicle, following driving based on a following distance, vehicle speed maintaining driving, a warning of collision of the vehicle, a warning of deviation of the vehicle from a lane, or the like.

In addition, the microcomputer 12051 can perform cooperative control intended for automatic driving, which makes the vehicle to travel autonomously without depending on the operation of the driver, or the like, by controlling the driving force generating device, the steering mechanism, the braking device, or the like on the basis of the information about the outside or inside of the vehicle which information is obtained by the outside-vehicle information detecting unit 12030 or the in-vehicle information detecting unit 12040.

In addition, the microcomputer 12051 can output a control command to the body system control unit 12020 on the basis of the information about the outside of the vehicle which information is obtained by the outside-vehicle information detecting unit 12030. For example, the microcomputer 12051 can perform cooperative control intended to prevent a glare by controlling the headlamp so as to change from a high beam to a low beam, for example, in accordance with the position of a preceding vehicle or an oncoming vehicle detected by the outside-vehicle information detecting unit 12030.

The sound/image output section 12052 transmits an output signal of at least one of a sound and an image to an output device capable of visually or auditorily notifying information to an occupant of the vehicle or the outside of the vehicle. In the example of FIG. 9, an audio speaker 12061, a display section 12062, and an instrument panel 12063 are illustrated as the output device. The display section 12062 may, for example, include at least one of an on-board display and a head-up display.

Figure 10:
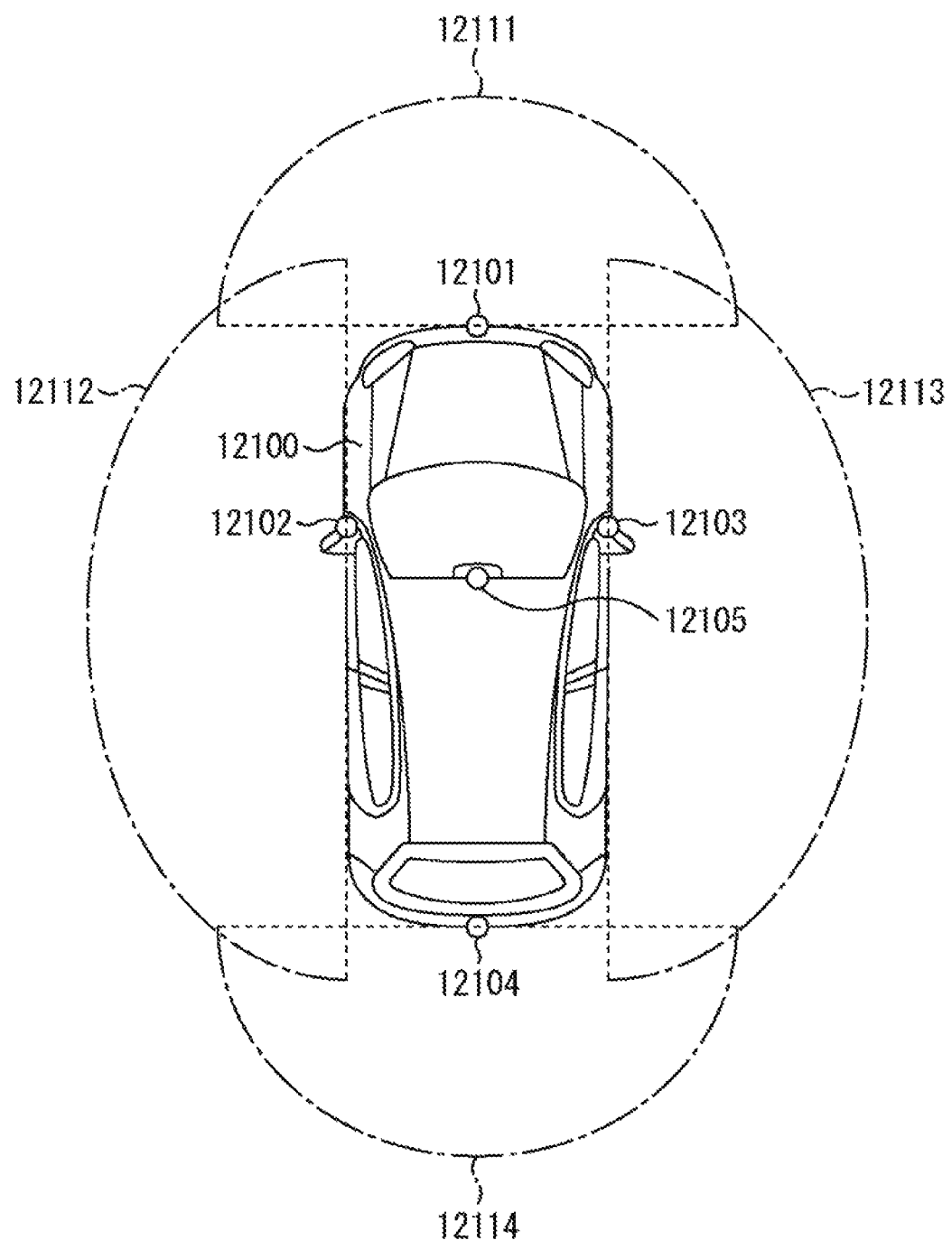
FIG. 10 is a diagram of assistance in explaining an example of installation positions of an outside-vehicle information detecting section and an imaging section.

FIG. 10 is a diagram depicting an example of the installation position of the imaging section 12031.

In FIG. 10, the imaging section 12031 includes imaging sections 12101, 12102, 12103, 12104, and 12105.

The imaging sections 12101, 12102, 12103, 12104, and 12105 are, for example, disposed at positions on a front nose, sideview mirrors, a rear bumper, and a back door of the vehicle 12100 as well as a position on an upper portion of a windshield within the interior of the vehicle. The imaging section 12101 provided to the front nose and the imaging section 12105 provided to the upper portion of the windshield within the interior of the vehicle obtain mainly an image of the front of the vehicle 12100. The imaging sections 12102 and 12103 provided to the sideview mirrors obtain mainly an image of the sides of the vehicle 12100. The imaging section 12104 provided to the rear bumper or the back door obtains mainly an image of the rear of the vehicle 12100. The images of the front obtained by the imaging sections 12101 and 12105 are used mainly to detect a preceding vehicle, a pedestrian, an obstacle, a signal, a traffic sign, a lane, or the like.

Incidentally, FIG. 10 depicts an example of photographing ranges of the imaging sections 12101 to 12104. An imaging range 12111 represents the imaging range of the imaging section 12101 provided to the front nose. Imaging ranges 12112 and 12113 respectively represent the imaging ranges of the imaging sections 12102 and 12103 provided to the sideview mirrors. An imaging range 12114 represents the imaging range of the imaging section 12104 provided to the rear bumper or the back door. A bird's-eye image of the vehicle 12100 as viewed from above is obtained by superimposing image data imaged by the imaging sections 12101 to 12104, for example.

At least one of the imaging sections 12101 to 12104 may have a function of obtaining distance information. For example, at least one of the imaging sections 12101 to 12104 may be a stereo camera constituted of a plurality of imaging elements, or may be an imaging element having pixels for phase difference detection.

For example, the microcomputer 12051 can determine a distance to each three-dimensional object within the imaging ranges 12111 to 12114 and a temporal change in the distance (relative speed with respect to the vehicle 12100) on the basis of the distance information obtained from the imaging sections 12101 to 12104, and thereby extract, as a preceding vehicle, a nearest three-dimensional object in particular that is present on a traveling path of the vehicle 12100 and which travels in substantially the same direction as the vehicle 12100 at a predetermined speed (for example, equal to or more than 0 km/hour). Further, the microcomputer 12051 can set a following distance to be maintained in front of a preceding vehicle in advance, and perform automatic brake control (including following stop control), automatic acceleration control (including following start control), or the like. It is thus possible to perform cooperative control intended for automatic driving that makes the vehicle travel autonomously without depending on the operation of the driver or the like.

For example, the microcomputer 12051 can classify three-dimensional object data on three-dimensional objects into three-dimensional object data of a two-wheeled vehicle, a standard-sized vehicle, a large-sized vehicle, a pedestrian, a utility pole, and other three-dimensional objects on the basis of the distance information obtained from the imaging sections 12101 to 12104, extract the classified three-dimensional object data, and use the extracted three-dimensional object data for automatic avoidance of an obstacle. For example, the microcomputer 12051 identifies obstacles around the vehicle 12100 as obstacles that the driver of the vehicle 12100 can recognize visually and obstacles that are difficult for the driver of the vehicle 12100 to recognize visually. Then, the microcomputer 12051 determines a collision risk indicating a risk of collision with each obstacle. In a situation in which the collision risk is equal to or higher than a set value and there is thus a possibility of collision, the microcomputer 12051 outputs a warning to the driver via the audio speaker 12061 or the display section 12062, and performs forced deceleration or avoidance steering via the driving system control unit 12010. The microcomputer 12051 can thereby assist in driving to avoid collision.

At least one of the imaging sections 12101 to 12104 may be an infrared camera that detects infrared rays. The microcomputer 12051 can, for example, recognize a pedestrian by determining whether or not there is a pedestrian in imaged images of the imaging sections 12101 to 12104. Such recognition of a pedestrian is, for example, performed by a procedure of extracting characteristic points in the imaged images of the imaging sections 12101 to 12104 as infrared cameras and a procedure of determining whether or not it is the pedestrian by performing pattern matching processing on a series of characteristic points representing the contour of the object. When the microcomputer 12051 determines that there is a pedestrian in the imaged images of the imaging sections 12101 to 12104, and thus recognizes the pedestrian, the sound/image output section 12052 controls the display section 12062 so that a square contour line for emphasis is displayed so as to be superimposed on the recognized pedestrian. The sound/image output section 12052 may also control the display section 12062 so that an icon or the like representing the pedestrian is displayed at a desired position.

An example of the vehicle control system to which the technology according to the present disclosure can be applied has been described heretofore. The technology according to the present disclosure is applicable to, for example, the imaging section 12031 or the like among the above-mentioned configurations.

It should be noted that embodiments of the present technology are not limited to the above-mentioned embodiments and various modifications can be made without departing from the essence of the present technology.

It should be noted that the present technology may also take the following configurations.

(1)

An image processing apparatus, including:

a first acquisition unit that acquires a first pixel signal output from a first pixel;

a second acquisition unit that acquires a second pixel signal output from a second pixel having a size smaller than that of the first pixel;

a temperature detection unit that detects temperature;

a composition gain determination unit that determines a composition gain corresponding to the detected temperature; and a composition unit that composes the first pixel signal and the second pixel signal multiplied by the composition gain.

(2)

The image processing apparatus according to (1) above, further including a pixel unit, a plurality of the first pixels and a plurality of the second pixels being arranged in the pixel unit.

(3)

The image processing apparatus according to (1) or (2) above, in which the first pixel and the second pixel have different temperature dependent characteristics.

(4)

The image processing apparatus according to any one of (1) to (3) above, further including a table that stores a temperature dependent correction amount in association with temperature, in which the composition gain determination unit acquires, from the table, the temperature dependent correction amount corresponding to the detected temperature, and calculates the composition gain by using the acquired temperature dependent correction amount.

(5)

The image processing apparatus according to any one of (1) to (3) above, further including a table that stores the composition gain in association with temperature, in which the composition gain determination unit acquires, from the table, the composition gain corresponding to the detected temperature.

(6)

The image processing apparatus according to any one of (1) to (5) above, further including:

a first signal processing unit that performs predetermined signal processing on the first pixel signal; and a second signal processing unit that performs predetermined signal processing on the second pixel signal, in which the composition unit composes the first pixel signal on which the predetermined signal processing has been performed and the second pixel signal on which the predetermined signal processing has been performed, the second pixel signal being multiplied by the composition gain.

(7)

The image processing apparatus according to (6) above, in which at least one of the first signal processing unit or the second signal processing unit performs OB (optical black) clamp processing corresponding to the detected temperature.

(8)

The image processing apparatus according to (6) or (7) above, in which at least one of the first signal processing unit or the second signal processing unit performs processing of multiplying a minimum gain corresponding to the detected temperature.

(9)

An image processing method for an image processing apparatus, including:

performing, by the image processing apparatus, a first acquisition step of acquiring a first pixel signal output from a first pixel;

a second acquisition step of acquiring a second pixel signal output from a second pixel having a size smaller than that of the first pixel;

a temperature detection step of detecting temperature;

a composition gain determination step of determining a composition gain corresponding to the detected temperature; and a composition step of composing the first pixel signal and the second pixel signal multiplied by the composition gain.

(10)

An electronic apparatus on which a solid-state image sensor is mounted, the solid-state image sensor including:

a pixel unit, a plurality of first pixels and a plurality of second pixels being arranged in the pixel unit, each of the plurality of second pixels having a size smaller than that of each of the plurality of first pixels;

a first acquisition unit that acquires a first pixel signal output from the first pixel;

a second acquisition unit that acquires a second pixel signal output from the second pixel;

a temperature detection unit that detects temperature;

a composition gain determination unit that determines a composition gain corresponding to the detected temperature; and a composition unit that composes the first pixel signal and the second pixel signal multiplied by the composition gain.

REFERENCE SIGNS LIST

11 pixel unit
12 imaging control unit
13 temperature detection unit
14 large-pixel-signal processing unit
15 large-pixel table
16 small-pixel-signal processing unit 17 small-pixel table
18 composition gain determination unit
19 composition table
20 composition unit

The invention claimed is:

1. An image processing apparatus, comprising:
a central processing unit (CPU) configured to:
acquire a first pixel signal output from a first pixel;
acquire a second pixel signal output from a second pixel having a size smaller than that of the first pixel;
acquire a temperature of a pixel unit that comprises the first pixel and the second pixel;
determine a composition gain corresponding to the acquired temperature; and
compose the first pixel signal, and the second pixel signal multiplied by the composition gain.

2. The image processing apparatus according to claim 1, further comprising the pixel unit, wherein
the pixel unit further comprises a plurality of first pixels and a plurality of second pixels,
the plurality of first pixels includes the first pixel, and
the plurality of second pixels includes the second pixel.

3. The image processing apparatus according to claim 2, wherein temperature dependent characteristics of the first pixel is different from temperature dependent characteristics of the second pixel.

4. The image processing apparatus according to claim 2, further comprising a table that stores a plurality of temperature dependent correction amounts in association with a plurality of temperatures, wherein the CPU is further configured to:
acquire, from the table, a temperature dependent correction amount corresponding to the acquired temperature, wherein
the plurality of temperature dependent correction amounts includes the acquired temperature dependent correction amount, and
the plurality of temperatures includes the acquired temperature; and
calculate the composition gain based on the acquired temperature dependent correction amount.

5. The image processing apparatus according to claim 2, further comprising a table that stores a plurality of composition qains in association with a plurality of temperatures, wherein
the CPU is further configured to acquire, from the table, the composition gain corresponding to the acquired temperature,
the plurality of composition gains includes the composition gain, and
the plurality of temperatures includes the acquired temperature.

6. The image processing apparatus according to claim 2, wherein the CPU is further configured to:
perform signal processing on the first pixel signal to generate processed first pixel signal;
perform signal processing on the second pixel signal to generate processed second pixel signal; and
compose the processed first pixel signal, and the processed second pixel signal multiplied by the composition gain.

7. The image processing apparatus according to claim 6, wherein the CPU is further configured to perform an OB (optical black) clamp processing operation, corresponding to the acquired temperature, on at least one of the first pixel signal or the second pixel signal.

8. The image processing apparatus according to claim 6, wherein the CPU is further configured to perform a multiplying operation of a minimum gain, corresponding to the acquired temperature, and at least one of the first pixel signal or the second pixel signal.

9. An image processing method, comprising:
in an image processing apparatus;
acquiring a first pixel signal output from a first pixel;
acquiring a second pixel signal output from a second pixel having a size smaller than that of the first pixel;
acquiring a temperature of a pixel unit that comprises the first pixel and the second pixel;
determining a composition gain corresponding to the acquired temperature; and
composing the first pixel signal, and the second pixel signal multiplied by the composition gain.

10. An electronic apparatus comprising:
a solid-state image sensor mounted on the electronic apparatus, wherein the solid-state image sensor comprises:
a pixel unit, wherein
the pixel unit comprises a plurality of first pixels and a plurality of second pixels, and
each of the plurality of second pixels having a size smaller than that of each of the plurality of first pixels; and
a central processing unit (CPU) configured to:
acquire a first pixel signal output from a first pixel of the plurality of first pixels;
acquire a second pixel signal output from a second pixel of the plurality of second pixels;
acquire a temperature of the pixel unit;
determine a composition gain corresponding to the acquired temperature; and
compose the first pixel signal, and the second pixel signal multiplied by the composition gain.

* * * * *